United States Patent [19]

Miwa et al.

[11] Patent Number: 4,790,321

[45] Date of Patent: Dec. 13, 1988

[54] METHOD OF DISPLAYING STREAM LINES OF AN INHOMOGENEOUS FLOWING MEDIUM AND A DEVICE THEREFOR

[75] Inventors: Hirohide Miwa, Kawasaki; Takaki Shimura, Machida; Tadahiko Yanashima, Fujisawa; Shinichi Amemiya, Yokohama, all of Japan

[73] Assignee: Fujitsu Limited, Kawasaki, Japan

[21] Appl. No.: 930,413

[22] Filed: Nov. 14, 1986

[30] Foreign Application Priority Data

Nov. 14, 1985 [JP] Japan .................................. 60-255401

[51] Int. Cl.$^4$ ............................................. A61B 10/00
[52] U.S. Cl. .............................. 128/660.07; 73/861.25
[58] Field of Search ................................ 128/660–663; 73/861.25, 625–626

[56] References Cited

U.S. PATENT DOCUMENTS

| 4,159,462 | 6/1979 | Rocha et al. ................. 128/661 X |
| 4,182,173 | 1/1980 | Papadofrangakis . |
| 4,271,842 | 6/1981 | Specht et al. ................. 128/661 |
| 4,448,200 | 5/1984 | Brooks et al. ................. 128/660 X |
| 4,476,874 | 10/1984 | Taenzer et al. . |
| 4,509,525 | 8/1985 | Seo . |
| 4,593,314 | 6/1986 | Siler ................. 128/661 X |
| 4,612,937 | 9/1986 | Miller ................. 73/861.25 |
| 4,660,565 | 4/1987 | Shirasaka ................. 128/660 |
| 4,679,565 | 7/1987 | Sasaki ................. 128/660 |

OTHER PUBLICATIONS

Machii et al., "Clinical Usefulness of Power-Mode Two-Dimensional Doppler Color Flow Mapping", WFUMB '85, p. 382.

Primary Examiner—Francis J. Jaworski
Attorney, Agent, or Firm—Staas & Halsey

[57] ABSTRACT

A method and device to display in real time a stream line of an inhomogeneous flowing medium such as blood flow in a heart, is disclosed. The object is scanned several times by ultrasonic beam pulses. Echoes appearing within a predetermined time interval at each point of the object are combined to produce an image of speckles formed by the flow. The process is repeated several times, to obtain the motion of the speckles. Differences between the images of spatially correlated speckles obtained within the time interval, produce the segments of the stream lines. Differences between successive frames or successive lines can be used to produce the speckle and several methods of scanning are disclosed to produce the differences between the images to produce the stream lines.

14 Claims, 7 Drawing Sheets

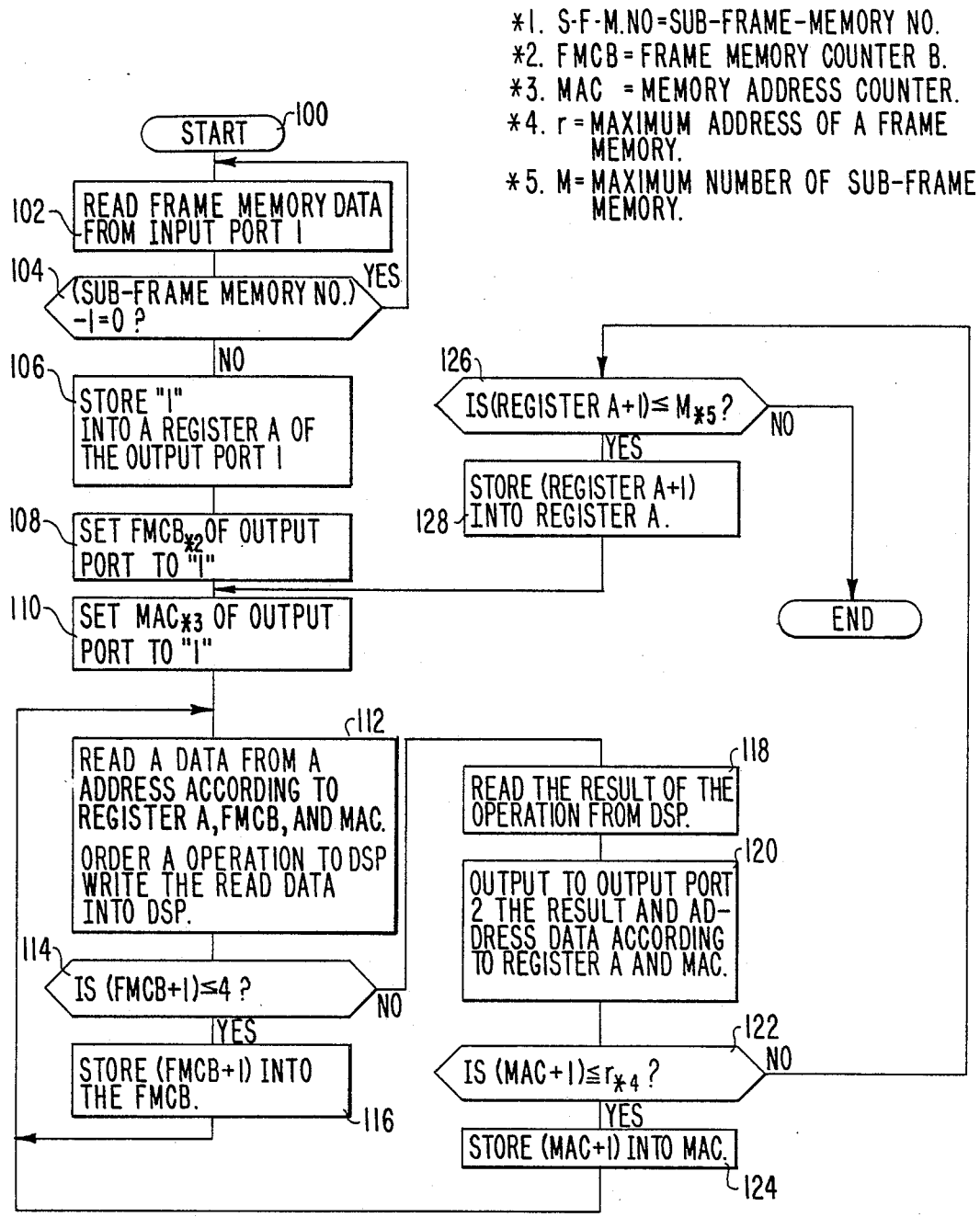

METHOD OF DISPLAYING STREAM LINES OF AN INHOMOGENEOUS FLOWING MEDIUM AND A DEVICE THEREFOR

CROSS REFERENCE TO RELATED APPLICATIONS

This application is related to U.S. application Ser. No. 789,921, filed Oct. 2, 1985, and assigned to the assignee of the present invention.

BACKGROUND OF THE INVENTION

1. Field of the Invention

This invention relates to a method of displaying, in real time, stream lins of an inhomogeneous flowing medium and a device therefor and, more particularly, to a device for displaying blood stream lines in a human heart in real time.

2. Description of the Related Art

In the art of medical electronics, an ultrasonic wave tomograph is used to display the conditions or motions of human organs on a cathode ray tube (CRT). Recently, Doppler tomography has been applied to the display of blood motion. This technique produces a flow map of blood as a two-dimensional tomogram using a color display. For example, a blood stream approaching a transducer, which generates and receives the ultrasonic pulse, is colored red and a stream travelling away from te transducer is colored blue, while the color tone is varied according to the speed of the blood stream. The speed of the blood stream is determined from a frequency shift, a phase shift or a distortion in the echo pulse caused by the Doppler effect associated with the moving blood. The process which obtains the speed of the moving body from the data is called a Doppler process, and hence, a tomograph using the process is called as a Doppler tomograph. The following U.S. Patents disclose the fundamentals of Doppler tomography intended for displaying blood flow: U.S. Pat. No. 4,182,173 to Papadeofrangakis et al, issued Jan. 8, 1980; U.S. Pat. No. 4,476,874 to Taenzer et al., issued Oct. 16, 1984; and U.S. Pat. No. 4,509,525 to Seo, issued Apr. 9, 1985.

In Doppler tomography, the measured speed of the blood flow is a relative speed of the blood in the scanning direction of the ultrasonic beam. The measured speed varies when the scanning direction is varied and, as a limit, the measured blood speed is zero when the blood stream is scanned orthogonally (perpendicular to blood flow direction). If the scanning direction is further rotated, the blood speed reverses.

An attempt to overcome the above problems has been proposed by K. Machii et al, in Proceedings of WFUMB '85, P. 382, in an article entitled "Clinical Usefulness of Power Mode Two Dimensional Doppler Colour Flow Mapping". The authors of the above paper detected a speed component of blood included in a Doppler tomogram obtained using a power echo of the ultrasonic beam. The application discovered is limited to a speed less than 0.1 m/s which is a very slow speed.

In addition, the prior art ultrasonic tomograph techniques cannot show blood stream lines. Essentially, blood stream lines are parallel to the blood vessel. In the past, the need to show blood stream lines has not been very high, however, recently, especially in the field of heart examination, it has become important to accumulate blood flow information on the heart. The heart is more like a chamber than a tube and it is not possible to anticipate the actual flow of blood from the appearance of the heart, especially of a ventricle. Accordingly, it has become important to display actual speed and direction, that is, blood stream lines in a tomogram. Until the present invention there has been no means available that can show the stream lines of blood flow in a human heart.

SUMMARY OF THE INVENTION

An object of the present invention is to provide a method for displaying stream lines of an inhomogeneous flowing medium.

Another object of the present invention is to provide a device for showing stream lines of the inhomogeneous flowing medium.

A further object of the present invention is to provide a tomograph which can show stream lines of blood flow in a human heart.

The present invention attains the above objects by using the motion of speckles which appear in a tomogram of an inhomogeneous flow such as blood stream. Two tomograms are taken at different times with a very short time interval therebetween during which a spatial correlation between the speckles is still retained. From an image made of the difference between the two tomograms, the motion, direction and speed of the speckles are obtained via a graphic process, and segments of stream lines are shown in the tomogram. When two tomographs are obtained within a very short time interval, there is insufficient time to scan the entire area of the scanning field. As a result, the present invention divides the scan field into m sub-fields, and in each of sub-fields, the abovementioned speckle processing is performed. When the processing in the first sub-field is completed, the next sub-field is processed, and in such a manner, the entire field is processed. According to the speed of flow and the required accuracy of stream line measurements, several methods of field separation and scanning are used.

Further objects and advantages of the present invention will be apparent from the following description, reference being had to the accompanying drawings wherein preferred embodiments of the present invention are clearly shown and like numerals refer to like parts throughout.

BRIEF DESCRIPTION OF THE DRAWINGS

FIG. 1 depicts various images of speckles taken within a short time interval, wherein:

FIG. 2 illustrates a first embodiment of the scanning method according to the present invention, wherein:

FIG. 9 is a flowchart of the process performed by CPU 400 in FIG. 7; and

DESCRIPTION OF THE PREFERRED EMBODIMENTS

First, a tomogram image produced from signals of ultrasonic pulses reflected from an inhomogeneous flowing body such as blood flow will be discussed. Blood is composed of a mixture of red blood corpuscles, hemoleukocytes and blood platelets immersed in blood serum. Mean density of blood is almost uniform at any point in the heart, for example. However, the microscopic spatial arrangement of the blood components, the red blood corpuscles, for example, are random. A reflection of an ultrasonic wave is composed of reflected or scattered waves produced by each of the red blood corpuscles, respectively. Since there reflected waves interfere with each other, each image obtained from the reflected waves includes speckles composed of randomly arranged white portions (that indicate strong reflections) and dark portions (that indicate weak reflections). Usually, the white portion is called a "speckle".

The reflection of the ultrasonic wave from blood is extremely weak compared to that of the muscles, the heart wall or the heart membrane. Blood reflections are not normally observed in an ordinary B mode image display, which indicates the intensity of the reflected wave as the brightness of an image on a CRT because the signal levels are too small. However, if two tomograms are taken in sequence and an image corresponding to the difference between the two tomograms is produced, the strong image components of the muscles and heart membrane, etc., which are not moving, disappear, and only the weak signals from a portion that has moved during the measurement is left on the display. In such an image, the image of the blood stream, and hence the speckles, appear strongly.

The size of the speckles produced by blood varies depending on the aperture of the transducer, the focusing of the beam, the depth of the reflecting body, the frequency of the ultrasonic wave, the bandwidth of the receiver, etc. In the following analysis, the shape of the speckle is approximated as a circle having a diameter of 5 mm, and the depth of measurement is assumed to be 10 cm.

Figure 1A:
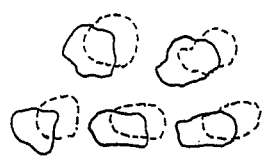
FIG. 1(a) is an example of speckle motion indicated by superposing two tomograms taken within a short time interval.

The formation of the segments of the stream lines will be described below. FIG. 1(a) is an image of speckles. In FIG. 1(a), two images of flowing speckles measured sequentially within a short time interval are superposed. The broken lines indicate the speckles observed by the first measurement, and the solid lines outline the same speckles observed by the second measurement. It is necessary that the time interval $\Delta T$ between the two measurements be very small, so that the images of the respective speckles obtained by the two measurements superpose each other, to retain the spatial correlation of the speckles. If $\Delta T$ is too large, the first (former) image of the speckles separates from the second (latter) image, and since the shape of the speckle varies rapidly, the correlation between the spoeckles is lost. It is also difficult to distinguish which speckle has moved to what location. Therefore, $\Delta T$ must be varied depending on the speed of the speckles to be measured.

Figure 1B:
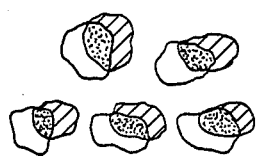
FIG. 1(b) is an image of the speckles made from a difference between the two tomograms in FIG. 1(a)

Let the image of FIG. 1(a) be shown with a brightness modulation, that is as a monochromatic image, and if an image of a difference in the brightness between the first and second images is created, it becomes as shown in FIG. 1(b). In the FIG. 1(b), the dotted portions have small differences in the brightness indicating the overlapped portion, the white portions indicate the difference has a positive value, and the hatched portions indicate the difference has a negative value. If the images are color modulated and the portions having a positive difference (white portions) are colored red and portions having a negative difference (hatched portions) are colored green, the central portions (dotted portions) becomes a mixture of red and green, as a result, it is possible to visually determine that the speckles have moved in a direction from green to red. The distance between the red and green portions corresponds directly to the speed of the speckles. Thus, it becomes possible to show the direction and speed of the blood stream using speckles with a small color mixture section indicating high speed.

As has been mentioned before, if $\Delta T$ is too large, the correlation between the first and second measurement images is lost, and it becomes impossible to judge the direction of motion of the speckles, in contrast, if $\Delta T$ is too small, the variation of the speckles becomes too small to show movement.

Figure 1C:
FIG. 1(c) is an image produced from the absolute value of FIG. 1(b)

If an absolute value of the brightness of FIG. 1(a) is shown, the image on the CRT becomes as shown in FIG. 1(c). On both ends of the speckles, the brightness is high, and at the center portion, the brightness is small. This picture resembles a photograph of moving particles taken with a long exposure time. The dislocation of the images shows the direction of motion, and the length of the dislocation shows the speed of motion.

Figure 1D:
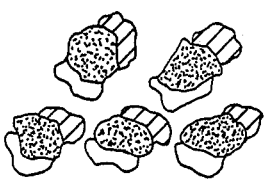
FIG. 1(d) is an image corresponding to FIG. 1(b) produced from three tomograms successively taken within short time intervals.
Figure 1E:
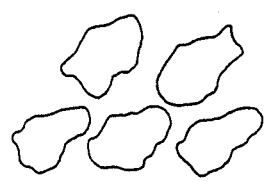
FIG. 1(e) is an image corresponding to FIG. 1(c) processed from the image of FIG. 1(d)

It is possible to repeat the above process several times. An example is shown in FIGS. 1(d) and 1(e). The FIGS. 1(d) and 1(e) show images obtained from two repetitions of the process, that is, the repetition number q is 2. In this example, three tomograms have been taken. Using the first and second, and second and third tomograms, the above process has been performed respectively, and each of the obtained images have been superposed on each other. FIG. 1(d) corresponds to FIG. 1(b), and the white portions become red, the hatched portions become green, and the dotted portions becomes a yellowish mixture of red and green. FIG. 1(e) corresponds to FIG. 1(c). FIG. 1(d) and 1(e) have the advantage that the images look more like segments of stream lines because they are longer.

Figure 1F:
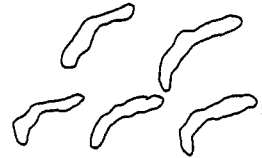
FIG. 1(f) is an image made by a thinning process applied to the image of FIG. 1(e) showing the segments of the stream lines.

Generally, the image of speckles are brightest at the center portion, and the image becomes darker as it approaches the periphery of the speckles. That is, the formed segments of the stream lines illustrated in FIG. 1(d) and FIG. 1(e) are brightest at the center and become darker on both sides of the images. Therefore, if the brightness is digitized using a threshold value comparison, that is, if the portions brighter than the threshold value are changed to maximum brightness (100% bright), and the portions in which brightness is less than the threshold value are changed to zero brightness, the images of FIG. 1(e) are thinned as shown in FIG. 1(f). compared to the broad lines of FIG. 1(d) and 1(e), the images of FIG. 1(f) more closely resemble the segments of stream lines.

As has been described before, it is necessary to retain the spatial correlation of speckles. When the speckle images of two tomograms are superposed as shown in FIG. 1(a), if a speckle observed by the first measurement (broken lines) contacts another speckle image, it will produce an error in the stream line or speed of flow. In practice, the diameter of a speckle is almost equal to the spacing between the speckles. As a result, the displacement of a speckle during the succeeding measurements must be less than the diameter of the speckle. This limits the maximum length of the segment of the stream line to be displayed on a tomogram to about twice the speckle diameter. For example, if the diameter of the speckle is 5 mm, the length of the stream line segment which can be shown in the tomogram, is less than 10 mm.

Therefore, the length of the stream line segments can be varied by varing the diameter of the speckles. The diameter of the speckles may be varied by varying the aperture of the transducer, the focusing of the beam and the wave length of the ultrasonic wave, etc. The most effective method of obtaining a long stream line is to introduce echo enhancing particles such as bubbles into the blood stream. Compared to the measurement using speckles, the particle (a bubble, for example) does not change its shape during motion, and the size and spacing between the particles may be controlled at will. The movement of bubbles may be traced without losing spatial correlation for a long period of time. This allows the repetition number q for the measurement to be increased to provide long stream lines compared to that of FIG. 1(f). It is similar to tracing the motion of a particle using a motion picture where the frames are superposed on each other.

Next, the conditions that $\Delta T$, the measurement time interval, should satisfy, will be considered. Let the expected maximum speed of the blood stream by V mm/ms, and the size of the speckle be D mm in diameter. In order to form a stream line, it is necessary to have at least an overlapped portion between the images of the same speckle when the first and second tomograms are superposed on each other. Therefore, it is necessary that $$V \cdot \Delta T < D \qquad (1)$$

If the size of each speckle is assumed to be equal to the spacing between them, the inequality (1) also becomes a condition required so that one speckle does not overlap another speckle. This also determines the maximum length of the stream line segments.

If the measurement is repeated q times to obtain more precise segments of the stream lines, the condition becomes $$V \cdot \Delta T \cdot q < D \qquad (2)$$

If artificial echo enhancing particles such as bubbles are introduced, it is possible to control the means spacing between the bubbles to be large as compared to the size of the bubble, therefore, the conditions of equations (1) or (2) become unnecessary.

Embodiments of the present invention will be disclosed with respect to a tomograph for displaying a blood stream in a human heart. For such a purpose, it is necessary to provide a measuring depth of at least 150 mm. Since the sound velocity in a human body is 1.5 mm/$\mu$s, it takes 0.2 ms for the ultrasonic wave to travel the distance 150 mm and return. It is also desirable to provide a frame rate of 15-30 frames/s to display the blood stream of a beating heart so that ordinary CRTs can be used. It is generally believed that the speed of an abnormal blood stream which flows backward from a gap in an incomplete cardiac valve sometimes increases up to 2.5 m/s. However, the embodiment discussed herein is designed to produce a display for a blood stream traveling up to 1 m/s. It is desirable to scan the object (the heart) with a fan shaped scanning field having a scan angle of 45°-90°, and display it as a frame on a CRT. It is also desirable to provide 64-128 scan lines per 90° for an ordinary B mode display.

Figure 2A:
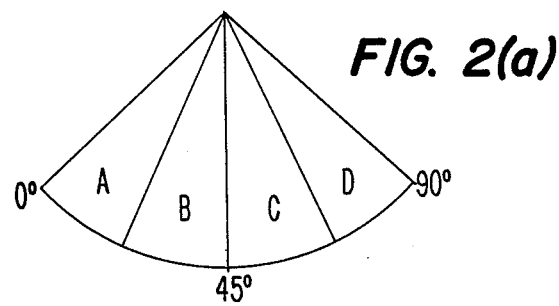
FIG. 2(a) shows division of the scanning field.
Figure 2B:
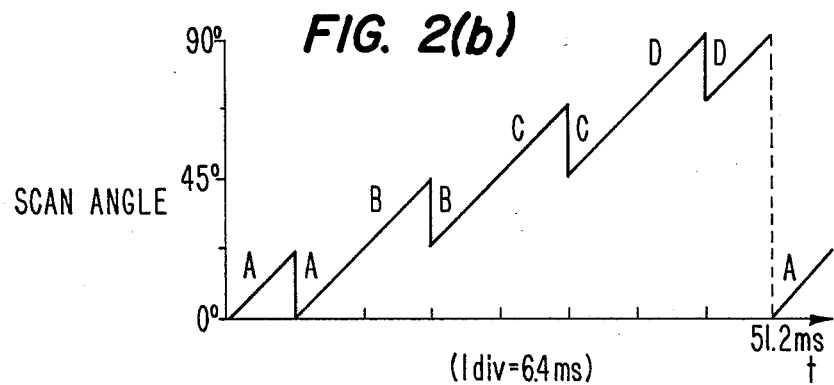
FIG. 2(b) depicts the time variation of the scan angles.

FIG. 2 shows a scanning method for an ultrasonic beam for a first embodiment. As shown in FIG. 2(a), a 90° scan field is divided into four sub-fields A, B, C and D, each having a angle of 22.5°. FIG. 2(b) shows a relationship between the scan angle and the time necessary to scan the entire frame of the scan field. The scan line density is 128 lines/90°, and each sub-field is scanned by 32 lines. As mentioned before, each scan line needs 0.2 ms, and it takes 6.4 (0.2×32) ms to scan one sub-field. Each sub-field is scanned at least twice, therefore, the measurement for one sub-field takes 12.8 ms. When a measurement for the sub-field A is finished, the next sub-field B is scanned successively. In this manner, 51.2 ms is required for measuring the entire 90° scan field. The frame rate becomes 20 frames/s, and the time interval between each scan $\Delta T$ becomes 6.4 ms. These measurement values satisfy the inequality (1).

The data collected for echo signals are successively stored in a memory, and after the measurement of one sub-field is completed, image processing is performed to obtain the segments of stream lines as has been described before. That is, if a substraction image, as in FIG. 1(b) is to be created, the data values for one scan line stored in the memory, are subtracted from the corresponding data values of a subsequent scan line stored in the memory and the results (the values of which indicate color) are converted into a color image. That is, once the data for each scan line is collected, simple mathematical operations are performed on data pairs where one item in the pair comes from one scan line and the other item comes from the succeeding scan line. If the absolute value or threshold comparison operations of FIGS. 1(c), 1(e) and 1(f) are to be performed, simple mathematical operations are performed on successive scan lines to obtain appropriate image values. However, the time required for such a process is very short compared to that required for the measurement of one sub-field. As a result, the image processing is completed for one subfield while the measurements for the next subfield are being completed, and the results are displayed on a CRT as a sub-frame. The images of the sub-fields obtained in such a manner are displayed successively on the CRT to construct the entire frame of the scanned field.

Figure 3:
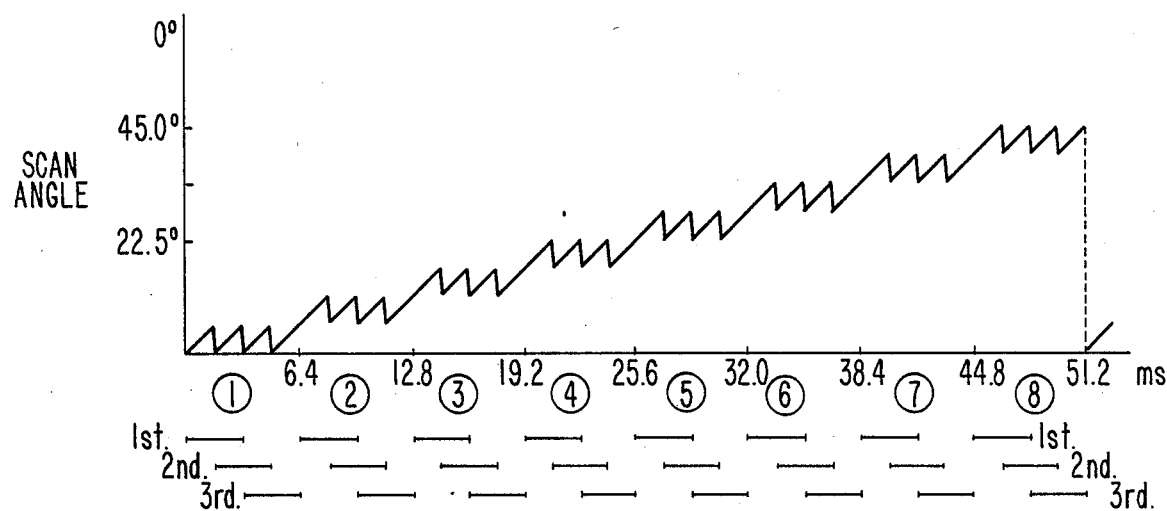
FIG. 3 illustrates a second embodiment of the scanning method, applicable to precise measurement and showing time variation according to scan angle.

A scan method for a second embodiment is shown in FIG. 3. This embodiment is appropriate to produce a more precise measurement of the stream line. The entire scan field of 45°, as compared to the 90° field of the prior embodiment, is divided into 8 sub-fields, and the measurements are repeated three times for each of the sub-fields, therefore, the repetition number q is 3. The scan line density remains 128 lines/90° as in the prior embodiment. The number of scan lines p which cover a sub-field is 8, and the time interval between each measurement $\Delta T$ becomes 1.6 ms (0.2×8). This embodiment allows a more precise stream line to be produced.

FIG. 3 shows a time variation of a scan angle of the ultrasonic beam. In FIG. 3, the ordinate is the scan angle and abscissa is time in milliseconds (ms). The small circled numerals along the abscissa indicate the sub-field being scanned. As shown in FIG. 3, each subfield is scanned four times. The small horizontal bars beneath the circled numerals indicate data pairs processed to obtain the difference between each in the pair for each sub-field, the first processing cycle is performed to obtain the difference in the first and second scan data, as indicated by the 1st bar. The second processing cycle is performed using the second and the third scan data, as indicated by the 2nd bar, and the third processing cycle is completed using the third and fourth scanning data indicated by the 3rd bar. For each processing cycle, the time $\Delta T$ is 1.6 ms. The images of the moving speckles are obtained respectively from the three processing cycles and the stream lines are obtained by superposing the three images produced. On the CRT, the sub-frames are each produced in 6.4 ms, and the total time to complete a frame is 51.2 ms, so the frame rate becomes approximately 20 frames/s.

In the second embodiment, compared to the first embodiment, $\Delta T$ the difference or time interval between the images to be processed is reduced to $\frac{1}{4}$. Therefore, the spatial wavelength of noise, induced by the slow motion of organs such as breathing or slippage of the transducer during measurement is reduced to $\frac{1}{4}$. As a result, it becomes well within the ordincary skill in the art to apply a filter to remove such noise, and hence, a better image is obtained.

A third embodiment of the scanning method is intended to suppress such noise to as low a value as possible. The time interval during which a difference is obtained, is reduced to 0.2 ms, that is, the difference is determined between successive shots of the ultrasonic beam. The scan field of 45° is divided into 8 sub-fields (m=8), and each sub-field is scanned by 8 scan lines respectively (p=8). Each scan line is scanned twice, and the echo information is obtained from the difference between the two shots. Therefore, the noise caused by the motion of the target is reduced to a minimum, and only the fast movement of blood flow remains. Such double scanning is repeated three times (q=3) for each sub-field.

Figure 4:
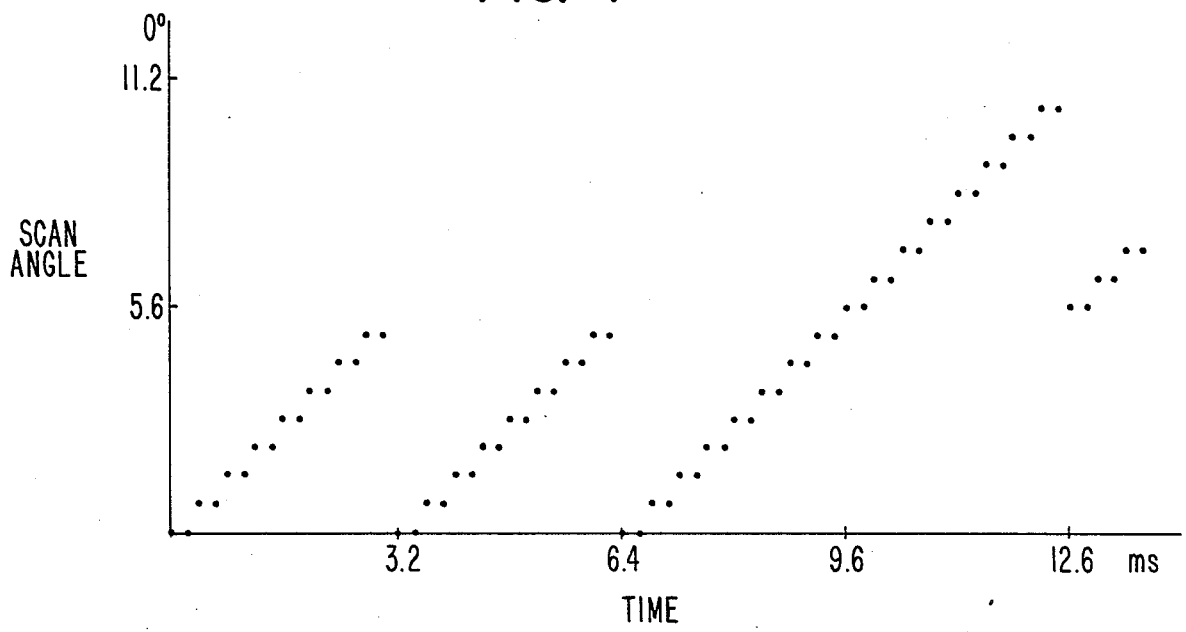
FIG. 4 illustrates a third embodiment of the scanning method used to reduce noise caused by motion of the target or applicable for measuring a very fast flow wherein small black dots indicate the transmission of the ultrasonic pulse at the respective angle.

FIG. 4 shows the time variation of the beam angle for the third method. The abscissa is time in milliseconds (ms), and the ordinate is the scan angle. Black dots indicate the shorts or transmissions of an ultrasonic beam pulse, therefore, each dot corresponds to one line scan, and from each of the two dots aligned horizontally is obtained the information for one scan line. Even though FIG. 4 shows only a part of the total scan, the scan angle is increased stepwise after each pair of dots. Each sub-field is scanned with eight double scans (it takes 3.2 ms), and the scanning is repeated three times for each subfield. When the process for one sub-field is completed (it takes 9.6 ms), the image is displayed on a CRT, and then the next sub-field is processed successively. The time for measuring one frame is 76.8 ms, so the frame rate becomes 13 frames/sec.

In practice, there often occur requirements for better images such that the total scan angle is required to be 90°, the frame rate 30 frames/sec, and the scanning line density should be 128 lines/90°. The above-described embodiments cannot satisfy such a wide beam requirement. In the application for heart clinics, for example, all the blood flow phenomena are repeated in synchronization with the heart beat/pulse. Accordingly, it is possible to apply stroboscopic technology to the method disclosed herein. For example, it is possible to provide an image of blood flow at a predetermined time phase against the R wave of an electro-cardiogram, by using measurements over several heart beats. For example, in the scanning method for the second or third embodiments, if the total scan angle is 22.5°, m=4, p=8, and q=3, the scan satifies the requirements for the scan line density and frame rate. Therefore, by adding four images each of 22.5°, each different from the other by 22.5°, respectively, taken from four successive cardiac pulses, it is possible to synthesize a 90° frame image. Such stroboscopic basic image synthesizing is well-known to the art and further description is omitted herein.

In the description of the above embodiments, the original signals from which the images are formed, are assumed to be simply an echo signal. In the art of ultrasonic imaging, various types of input signals are available, for example, a time gain controlled signal, a logarithmic signal, an orthogonally detected signal, a power signal and so on. The present invention does not exclude the use of such signals as its input.

It will be clear to those of ordinary skill in the art that the above-described embodiments of the scanning methods are used to accumulate the information concerning reflections of ultrasonic waves. Therefore, various modifications are possible, for example, scanning several times on the same line to reduce noise, and after reduction of noise, the signal is used as the signal of a scan line. The above-disclosed embodiments are, therefore, to be considered in all respects as illustrative and not restrictive.

Figure 5:
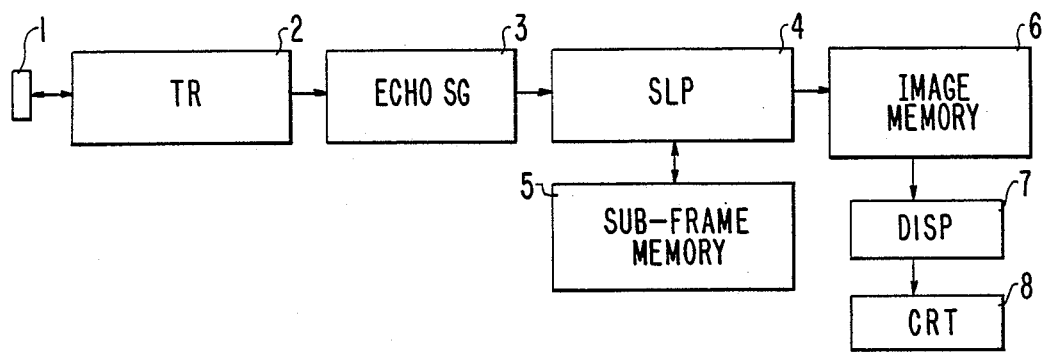
FIG. 5 is a block diagram showing a circuit of an ultrasonic tomograph device embodying the present invention.

A device configuration of a tomograph that will realize the above-discussed measurements is shown in FIG. 5. A transducer 1 emits and receives the ultrasonic beam, and a transmit/receive circuit 2 transmits and receives the ultrasonic wave. A transducer 1 and a transmit/receive circuit 2 used in a well-known ultrasonic imaging device having a B mode display are appropriate for use in the present invention. An echo signal generator (ESG) 3 processes the received echo signal and generates a signal having various characteristics suitable for obtaining a desired image, for example, a logarithmic wave, a gain controlled echo signal, a power signal, etc. As has been described above, the device can use any of the above-mentioned signals. Suitable generatores are all well-known in the art of B mode display, so further description is omitted herein for simplicity.

The signal processed by the echo signal generator 3 is an analog signal and is converted to a digital echo signal by an analog to digital converter (A/D converter) included in the generator. The digital echo signal is supplied to a stream line processor (SLP) 4. The stream line processor stores the echo signals in a sub-frame memory 5, and reads out the contents of the memory 5 and processes same as has been described before to provide image signals. The image signals are stored in an image memory 6. A display circuit (DISP) 7 reads out the contents of the image memory, and displays same on a CRT 8 using the display data for each image point to determine the color of a corresponding point on the CRT 8.

The operation of the stream line processor (SLP) 4 will be described with respect to FIG. 6. The echo signal processed in the echo signal generator 3 is digitized and supplied to the SLP 4. The SLP 4 includes a digital scan converter (DSC) 41, which provides the input signal with an address indicating where it is to be stored in the sub-frame memory 5. The sub-frame memory 5 includes a plurality of memories respectively first, second and third sub-frame memories and so on (51, 52, 53, . . . ), corresponding to the number of sub-frames m which divide the scan field. The SLIP 4 also includes switches S1, S2, S2, etc., respectively, corresponding to the sub-frame memories. The switche switch the flow of address and echo signals to the sub-frame memories or from the memories to a digital signal processor (DSP) 42. The I/O (input and output) ports of the circuits and data bus lines connecting them are identified by notations A and D, indicating an address bus and a data bus, respectively. The direction of data flow in the data buses are indicated by arrows.

Figure 6:
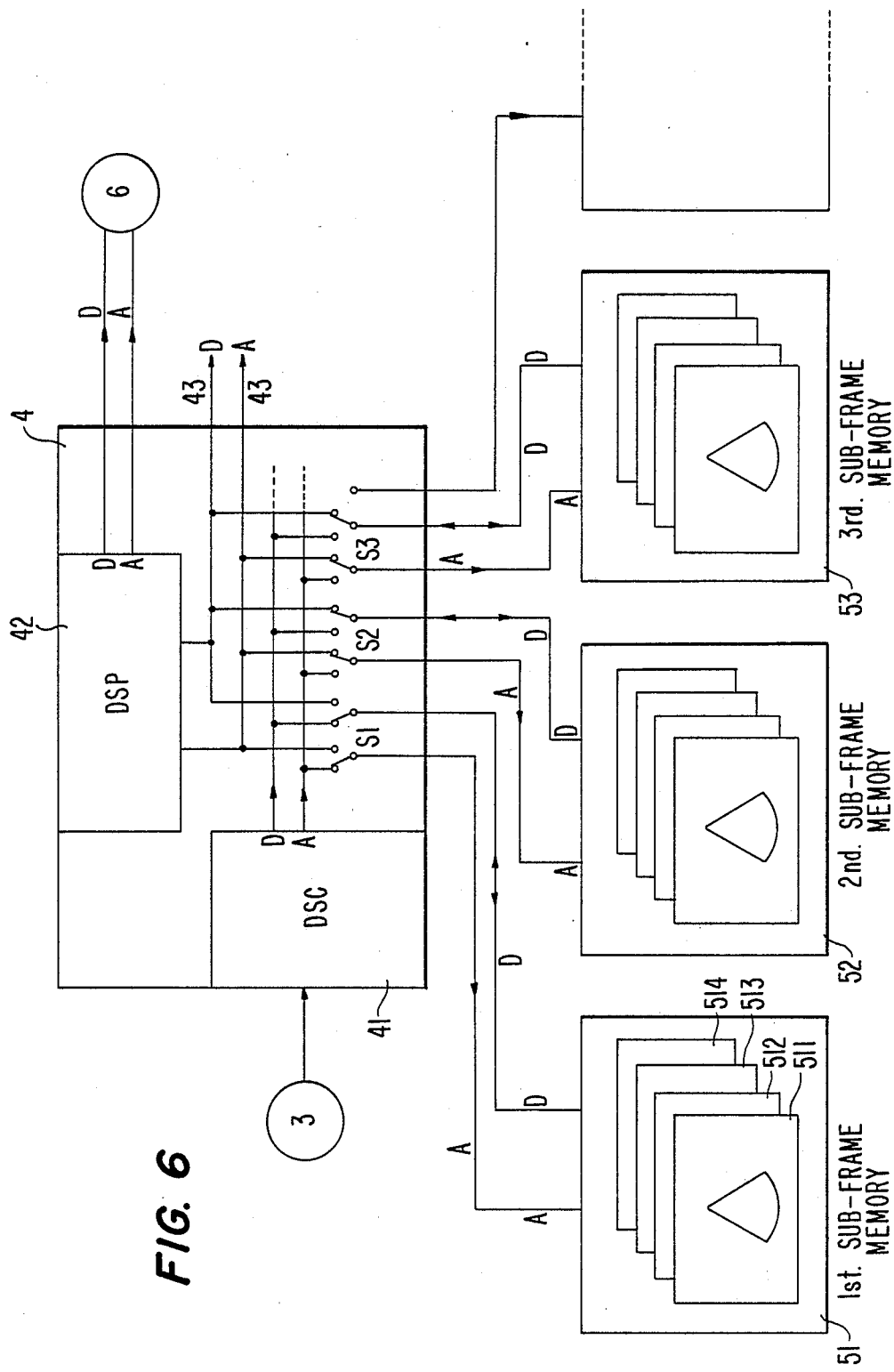
FIG. 6 is a block diagram of a stream line processor 4 and sub-frame memories 51, 52 and 53 illustrating their operation in the circuit of FIG. 5.

For example, when the beam is scanning the first sub-field, the switch S1 is switched to the DSC side, and the other switches are switched to the DSP side, as shown in FIG. 6. The echo data is stored in the first sub-frame memory 51. In the first sub-frame memory 51, echo data samples are stored in memory planes 511, 512, 513 each corresponding to the first, second, third scans. During this time period, the other switches are switched to the DSP side, so that the DSP 42 can perform the processes necessary to obtain the stream line data using the data stored in the second and third sub-frame memories, etc. The data processed by the DSP 42 are sent to the image memory 6 and stored therein.

When the scanning for the first sub-frame is completed, the switches S1 and S2 are switched respectively to the DSP and DSC sides. The echo data are stored in the second sub-frame memory 52, and the data stored in the first sub-field memory 51 are processed by DSP 42. In a like manner, the entire field is scanned and processed successively. The digitial signal processor DSP 42 is preferably an MB8764 processor chip available from Fujitsu of Japan or a µPC7720 or a TM32020 from NEC or Texas Instruments, respectively.

Figure 7:
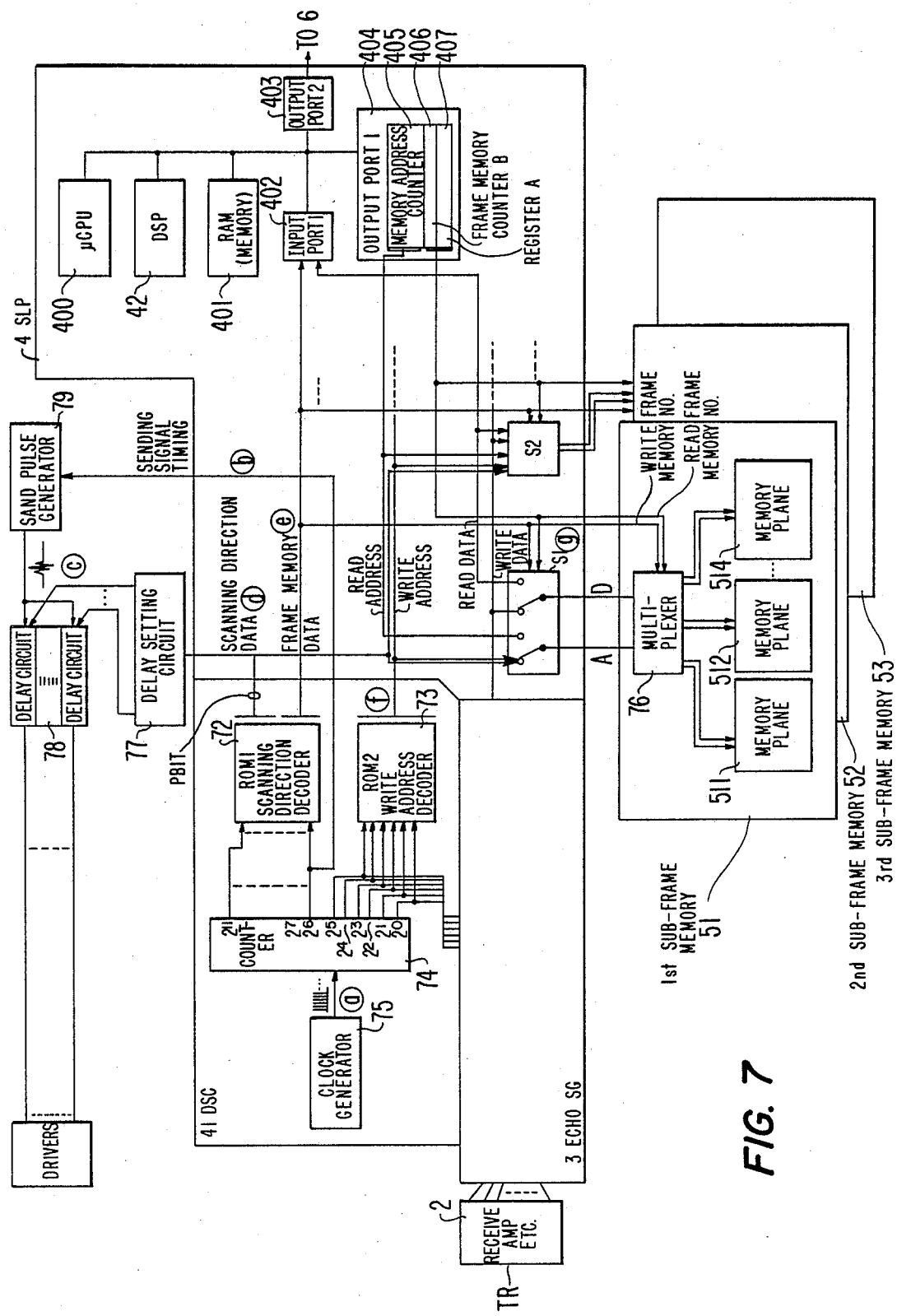
FIG. 7 illustrates the stream line processor 4 in greater detail.

The details of the components of FIG. 6 are shown in FIG. 7. The SLP 4 includes a micro CPU 400 and controls timing and switching. The digital scan converter 41 (DSC), includes ROM1 (72), ROM2(73), a counter 74 and a clock generator 75. Each of the sub-frame memories 51, 52—(only 1st sub-frame memory 51 is shown in detail) includes a multiplexer 76 and memory planes 511 . . . 514.

Figure 8:
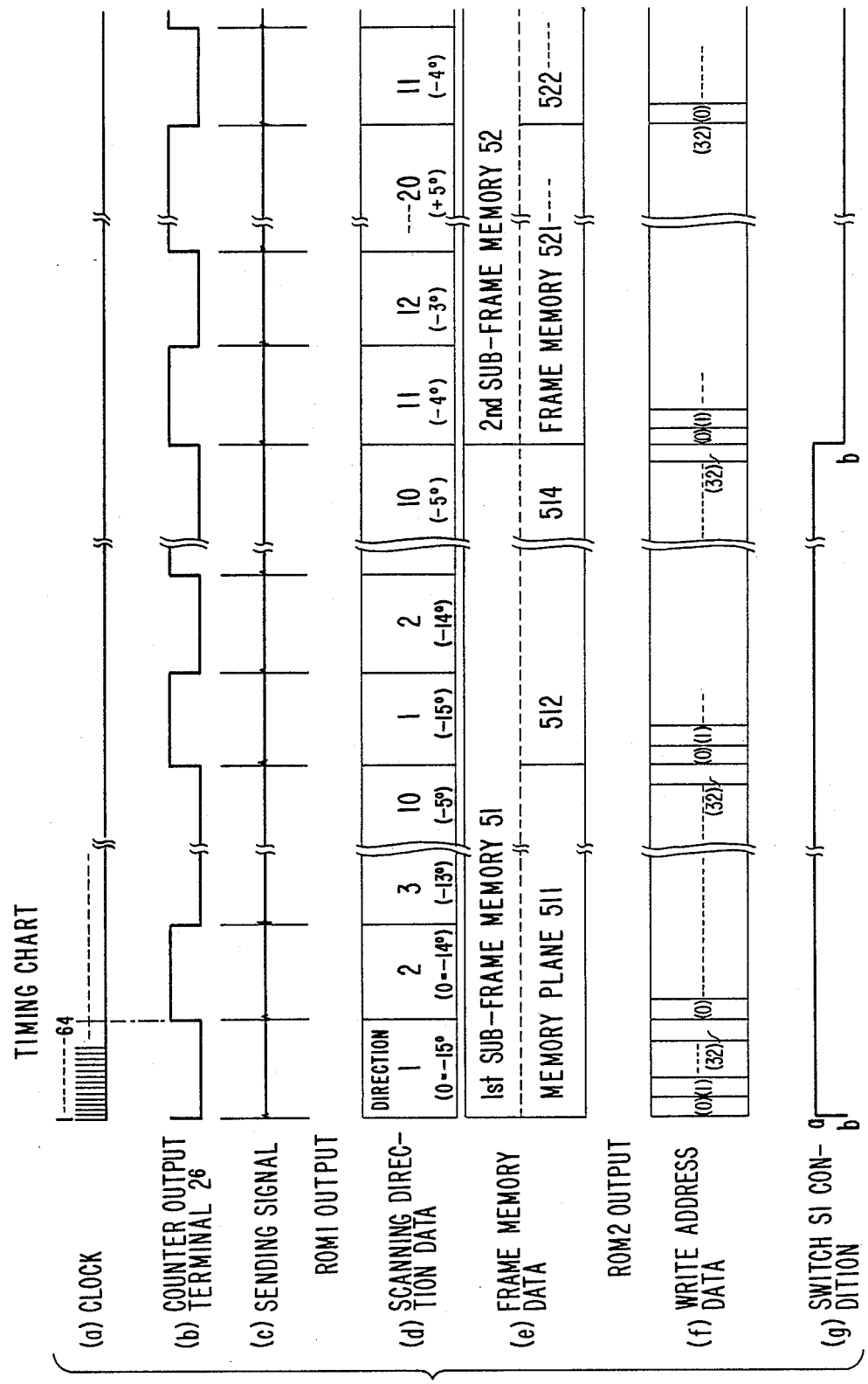
FIG. 8 is a timing chart of the stream line processor 4.

A timing chart for FIG. 7 is shown in FIG. 8. The timing of the system is synchronized to clock pulses generated by the clock generator 75 the output waveform of which is shown in FIG. 8 $(a)$. The counter 74 has n output terminals respectively, for ROM1 and ROM2 corresponding to the $2^0$ and to $2^n$ outputs. In the preferred embodiment, the number n is 10, therefore, the circuit has 10 terminals for data for the ROMs. As an example, the output signal from the terminal $2^6$ is shown in FIG. 8 $(b)$. A pulse sending signal 8 $(c)$ synchronized to the output signal of 8 $(b)$ ), activates the transmit portion of the transmit/receive circuit 2. Read addressed for ROM1 and ROM2 are supplied by the counter 74. The received echo signals are converted to digital signals by the echo signal generator (ESG) 3 and stored in respective memory planes 511, 512 . . . 514. The address where each sample is stored is determined by the scanning direction decoder ROM1 72 and the write address decoder ROM2 73. The output data produced by ROM1 72 is shown in 8 $(d)$ and 8 $(e)$, while the output data produced by the ROM2 73 is shown in FIG. 8 $(f)$. As can be seen, ROM1 72 determines scan direction, subframe memory and memory plane, while ROM2 73 determines location within the selected memory plane. The output data 8 $(d)$ specifies a scanning direction and is used to set pulse delay times in a delay set circuit 77 for delay circuits 78. Conventional phase delay techniques are used to direct the scanning beam. In this embodiment, the scan direction $\theta$ is directed from $-15°$ to $-5°$ for the first sub-frame memory, and from $-4°$ to $+5°$ for the second sub-frame memory, and so one, for each corresponding acan subfield 1 to 10. The scan for each sub-field is repeated four times, as previously discussed and then the scan is shifted to the next sub-field. The output data 8 $(e)$ depicts frame memory data which includes data for designating sub-frame memories 51, 52 . . . , and data for designating the memory planes 511, 512, . . . 514, 521 . . . 524, etc., in each of the sub-frame memories, as discussed with respect to FIGS. 3, 6 and 7. The output 8 $(f)$ of the ROM2 73 indicates the address (memory location) where the data should be stored in the selected memory plane. The write address data from ROM1 72 and ROM2 73 are sent to all of the memory planes simultaneously, with the frame and plane data controlling switches S1 and S2 for data routing to the appropriate sub-frame memory.

The switch S1 and multiplexer 76 select one of the frame memories in each sub-frame memory according to the memory plane data 8 $(e)$. The timing of the switch S1 is shown in 8 $(g)$. As can be seen in the figures, the switch S1 is switched to a or b after four sub-field scans. The switching of the switches S2, S3 . . . are similar to that of S1.

A data flow cycle in the circuit of FIG. 7, begins when a change occurs in the output signal from the output terminal $2^6$, indicating pulse send time, and a pulse is produced by the send pulse generator 79. At this time, the output of the ROM1 72 indicates a scan direction 1 which indicates the angle at which to transmit an acoustic pulse. The delay setting circuit 77 selects the delay time for each delay circuits 78 based on the scan direction data. An ultrasonic pulse is transmitted by a transducer 1 in a predetermined direction 1 ($\theta = -15°$ in this embodiment). During this period, the output of the ROM1 selects the 1st sub-frame memory 51 and memory plane 511 as the unit where the received data should be stored, and the output of ROM2 selects the write address (0)~(n) or storage location according to the value of the outputs $2^0$~$2^5$ of the counter 74. The location address data is supplied to the memory plane 511 through the switch S1 and the multiplexer 76. The output of the echo signal generator 3 is also supplied to the memory plane 511 and stored in the location designated by the address data.

In such manner, plural scan data is stored for one scan line, and when the line scan is finished, the ROM1 72 outputs the direction 2 ($\theta = -14°$). The scan direction is changed every 64 clock pulses, with a step increment of 1° in the preferred embodiment, and after the scanning is repeated n times and a sub-field scan is completed. Next, the ROM1 72 selects the next memory plane 512, and the same process, as described above, is repeated. In the preferred embodiment, the sub-field scan is repeated four times, each time varying the selected memory plane (511~514) in which the data is stored, after which the scanning for the first sub-field is complete. Then, ROM1 72 selects the 2nd sub-frame memory, at the same time, designates a direction n+1~2n, corresponding to a scan direction of $\theta = -4 \sim +5$.

During the above-described sub-field scan, the switch S1 is switched to the terminal a and when the scanning for the 1st sub-field is completed, S1 is switched to the terminal b to read out and store data in the image memory 6 of FIG. 5. At the same time, the switch S2 is switched to the terminal so that scan data can be stored in sub-frame memory 52. The scan and data storage for the 2nd sub-field and the successive sub-fields are done in a manner similar to that for the 1st sub-frame.

Figure 10:
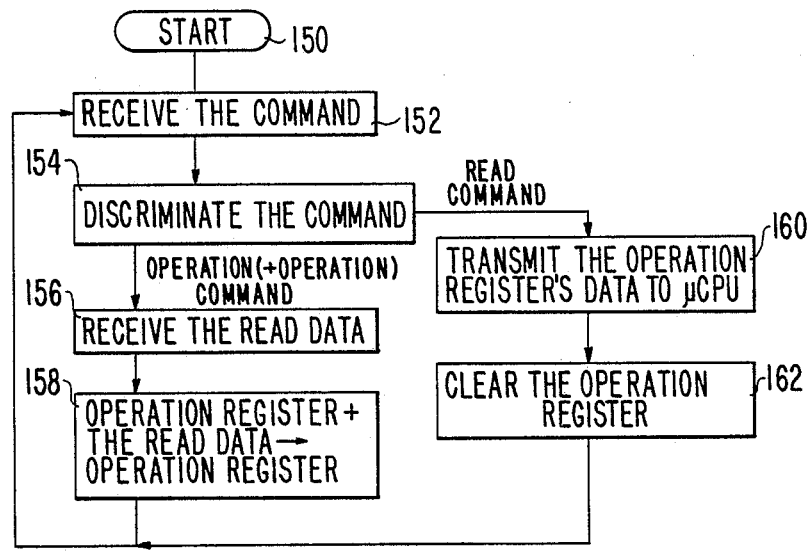
FIG. 10 is a flowchart of the operations performed by the digital signal processor 42.

A flowchart illustrating the steps performed by micro CPU 400 is illustrated in FIG. 9. The micro CPU 400 reads 102 frame receiver. memory data 8 ⓔ from an input port 1 (402) which is connected to the ROM1 72. Then, the miro CPU 400 selects the data indicating the sub-frame memory from the read data, and substracts "1" from the selected data. If the result 104 is "0", the micro CPU 400 repeats the first and second steps. The first and second steps are to determine start timing for the operation. "0" indicates that the data storing operation should be done for a sub-frame memory other than the 1st sub-frame memory. If the correct sub-frame is the 1st sub-frame, the micro CPU 400 stores 106 the number "1" into a register A (407) in the output port 1 (404). The data in register A (407) indicates the data storage sub-frame memory. Next, the micro CPU 400 loads 108 "1" into a frame memory counter B (406) which designates one of the memory planes in the selected sub-frame memory. Then, the micro CPU 400 loads 110 "1" into a memory address counter 405 which designates a memory address location in the selected memory plane. The micro CPU 400 proceeds to read 112 the data from the addressed location of the memory plane in accordance with the data stored in the register A (4-07), frame memory counter B (406) and the memory address counter (405), then, the micro CPU 400 supplies the DSP 42 with an operation command directing the DSP to store the read data into the DSP 42. The micro CPU 400 reads the data in the frame memory counter B (406), and adds "1" to determine 114 whether the data is smaller than "4". Where "4" is equal to the number of the memory planes includes in one sub-frame memory. This determines whether the micro CPU 400 has read all of the memory planes in the sub-frame memory. If the result is "Yes", the micro CPU 400 increments 116 the frame memory counter B (406) to change the selected memory plane, after that, repeats the above-mentioned steps. If the result if "no", the micro CPU 400 provides 118 the DSP 42 with a "read command". Then, the DSP 42, the process of which is shown in FIG. 10, supplies 118 the micro CPU 400 with the result of the operation. The micro CPU 400 then supplies 120 the output port 2 (403), which is connected to the image memory 6, with the result, the address data of the sub-frame memory in the register A (407) in which the data are stored, and the data in the memory address counter 405.

The micro CPU 400 reads the address data from the memory address counter 405, then adds "1" to the read data and after that, determines 122 whether the result is smaller than the address number "r" which is the maximum address of one memory plane. If the result is "yes", the micro CPU 400 increments 124 the memory address counter 405, and then repeats the above-discussed steps. If the result is "no", then micro CPU 400 has read all of the memory locations in the memory plane in one sub-frame memory, as designated by the register A (407). Then the micro CPU 400 increments the sub-frame memory of the register A (407), and determines 126 whether the result is smaller than "m" the maximum number of sub-frame memories. If the result is "yes", the micro CPU increments 128 the register A to change the selected sub-frame memory, and then, repeats the above-discussed steps so that the micro CPU 400 is able to provide the image memory 6 with the image processing results relating to all of the sub-frame memories. If the result is "No", the micro CPU 400 has finished the process.

FIG. 10 is a flow chart of the operation of the digital signal processor DSP 42. The DSP 42 starts after receiving 152 a command and determines 154 the type of command received. If the received command specifies an add operation, the DSP 42 accepts 156 the data and adds the received data to data stored in an operation register in the DSP 42. If the received command is the read command, the DSP 42 transmits 160 to the micro CPU 400 the data stored in the operation register and clears 162 the operation register. The above-discussion of the DSP 42 indicates that the DSP 42 is performing an adding operation on each piece of received data, however, the DSP can perform any of the common mathematical operations, such as multiply, subtract, obtain absolute value, etc. under the command of the micro CPU 400 to perform the operations necessary to obtain the speckle superposition images of FIG. 1.

The display process for displaying the image stored in the image memory 6 on the CRT 8 using a display circuit 7, is very popular and well-known in the art, so the description thereof is omitted for simplicity. It is usually necessary to create a display superposing the stream line segments and the image of the target (the heart, for example). For such a purpose, the echo data obtained directly from the data bus 43, 43' (FIG. 6) can be used. The data includes the image information for the target. Mixing the target data with the data stored in the image memory 6 is a very popular and well-known process.

As has been described, it is possible to display in real time the segments of stream lines of a blood stream in a heart. This disclosure has been provided with respect to an application to blood flow, but it is obvious that the invention may be applied to any other inhomogeneous flow. The presently disclosed embodiments are, therefore, to be considered in all respects as illustrative and not restrictive, the scope of the invention being indicated by the appended claims, rather than the foregoing description, and all changes which come within the meaning and range of equivalency of the claims are, therefore, to be embraced therein.

What is claimed is:

1. A method for displaying in real time a stream line of an inhomogeneous flowing medium by tracing motion of speckles appearing in tomograms taken sequentially and separated by a predetermined time interval, said method comprising the steps of:
   (a) scanning an object in which said inhomogeneous flowing medium is situated by sending out pulses of an ultrasonic wave beam to scan the object plural times within a predetermined time interval;
   (b) forming images of the speckles by combining a first echoe of one of said speckles with a second echo of said one of said speckles taken after said first echo but within said time interval; and
   (c) obtaining graphic images of a trajectory of said speckles by producing and displaying an image corresponding to a difference between the two echoes of the same speckle.

2. A method according to claim 1, wherein said tomograms are performed on a scan field of said object and said scan field is divided into m subfields and steps (a)–(c) are performed for each of said sub-fields.

3. A method according to claim 2, wherein the scanning in step (a) is a frame scan, the time interval is the period of the frame scan, and step (b) is performed by producing a difference between each of the corresponding scan lines of two succeeding frames.

4. A method according to claim 2, wherein said scanning in step (a) is a line scan, the time interval is a period of a line scan, and step (b) produces a difference between two successive scan lines.

5. A method according to claim 2, wherein said inhomogeneous flowing medium is blood in a living body, and steps (a)–(c) are performed for each heart beat pulse successively for said sub-field.

6. A method according to claim 5, wherein said time interval is $\Delta T$, and wherein $\Delta T$, a mean diameter D of said speckles and a maximum velocity V of the blood flow satisfy the following relationship:

$$V \cdot \Delta T < D.$$

7. A method according to claim 1, further comprising the step of (d) comparing the value of said difference obtained in step (c) with a threshold value, and setting the difference to a predetermined maximum or minimum in dependence on the comparison.

8. A method according to claim 1, further comprising means for producing an absolute value image of the stream line image and displaying only those portions of the stream line image which have a brightness above a threshold.

9. A device for displaying in real time, on a cathode ray tube, a stream line of an inhomogeneous flowing medium by scanning an object in which said inhomogeneous flowing medium is situated with ultrasonic wave beam pulses and processing echoes thereof reflected from the object, said device comprising:
   transducer means for converting electrical energy to ultrasound energy and vice versa and for sending out ultrasound beam pulses and receiving the echoes;
   transmitting and receiving circuit means, operatively connected to said transducer means, for exciting the transducer means to generate the beam pulses so as to scan the object plural times within a predetermined time interval, receiving echo signals from the transducer and converting the echo signals into electrical signals;
   echo signal generator means, operatively connected to said transmitting and receiving circuit means, for processing the electrical signals and for providing a digital echo signal suitable for image processing;
   sub-frame memory means for storing the digital echo signal;
   stream line processor means for processing the data stored in said sub-frame memory means to obtain data of segments of stream lines;
   image memory means for storing the data of the segments of the stream lines; and
   display means for retrieving the data stored in said image memory means and generating an image signal for the segments of stream lines to display on the cathode ray tube.

10. A device according to claim 9, wherein said sub-frame memory means comprises plural memory planes for storing the digital echo signals.

11. A device according to claim 9, wherein said stream line processor comprises:
   digital scan conversion means, operatively connected to said echo signal generator and said sub-frame memory means, for providing the digital echo signal with an address for a storage location in said sub-frame memory means;
   digital signal processing means, operatively connected to said sub-frame memory means and said image memory means, for combining digital echo signals appearing within said time interval to obtain an image of a speckle, and providing a difference between the speckles of different time intervals; and
   switches connected to said digital scan conversion means, said digital signal processing means and said sub-frame memory means to control the flow of data and addresses between said digital scan conversion means, said digital signal processing means and the sub-frame memory means.

12. A device according to claim 11, wherein said digitial signal processing means compares the value of said difference between the speckles with a threshold value, and sets the difference to a predetermined maximum or minimum value in dependence on the comparison.

13. A device according to claim 9, wherein said time interval is $\Delta T$, and wherein $\Delta T$, a means diameter D of said speckles and a maximum velocity V of the flood flow satisfy the following relationship:

$$V \cdot \Delta T < D.$$

14. A method of displaying stream lines in an inhomogeneous flowing medium, comprising the steps of:
   (a) repetitively scanning the medium with an ultrasonic beam;
   (b) obtaining stream line images by substracting an echo image of a first beam scan from an echo image of a second scan; and
   (c) displaying the stream line images.

* * * * *

UNITED STATES PATENT AND TRADEMARK OFFICE
CERTIFICATE OF CORRECTION

PATENT NO. : 4,790,321

DATED : December 13, 1988

INVENTOR(S) : Miwa et al.

It is certified that error appears in the above-identified patent and that said Letters Patent is hereby corrected as shown below:

Col. 1, line 15, "lins" should be --lines--.

Col. 2, line 35, "abovementioned" should be --above-mentioned--.

Col. 8, line 34, "to" should be --in--;
      line 68, "generatores" should be --generators--.

Col. 9, line 27, "SLIP" should be --SLP--;
      line 29, "switche" should be --switches--.

Col. 10, line 11, delete ")";
      line 33, "acan" should be --scan--.

Col. 11, line 34, delete "receiver.".

Col. 12, line 2, "if" should be --is--.

Signed and Sealed this

Eleventh Day of July, 1989

Attest:

DONALD J. QUIGG

Attesting Officer      Commissioner of Patents and Trademarks